US00PP11621P

United States Patent [19]

Noodelijk

[11] Patent Number: Plant 11,621

[45] Date of Patent: Nov. 7, 2000

[54] CHRYSANTHEMUM PLANT NAMED 'REFOCUS'

[75] Inventor: Robert Noodelijk, Woubrugge, Netherlands

[73] Assignee: Chrysanthemum Breeders Association N.V., Netherlands

[21] Appl. No.: 09/149,300

[22] Filed: Sep. 9, 1998

[51] Int. Cl.[7] ..... A01H 5/00

[52] U.S. Cl. ..... Plt./286

[58] Field of Search ..... Plt./286, 298

*Primary Examiner*—Howard J. Locker
*Attorney, Agent, or Firm*—Parkhurst & Wendel, L.L.P.

[57] ABSTRACT

A chrysanthemum plant named Refocus characterized by its small sized blooms with purple ray florets and green-yellow disc florets.

2 Drawing Sheets

The present invention is related to the plants in the following co-pending applications:

| Application no. | Filing Date | Title |
|---|---|---|
| 09/149,299 | 29/09/98 | Pink Refocus |
| 09/149,460 | 09/09/98 | Red Refocus |
| 09/149,657 | 09/09/98 | White Refocus |

BACKGROUND OF THE INVENTION

The new plant of the present invention comprises a new and distinct cultivar of chrysanthemum plant that was discovered and selected as one flowering plant within the progeny of a cross of a female parent chrysanthemum cultivar named 'Recette' (not patentd) and a male parent chrysanthemum named 'Rex' (not patented) by Rob Noodelijk in May, 1992.

The first act of asexual reproduction of Refocus was accomplished when vegetative cuttings were taken from the initial selection in August, 1992 in a controlled environment in Ter Aar, Holland.

SUMMARY OF THE INVENTION

The present invention is a new and distinct variety of chrysanthemum bearing small sized blooms with purple ray florets and green-yellow disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
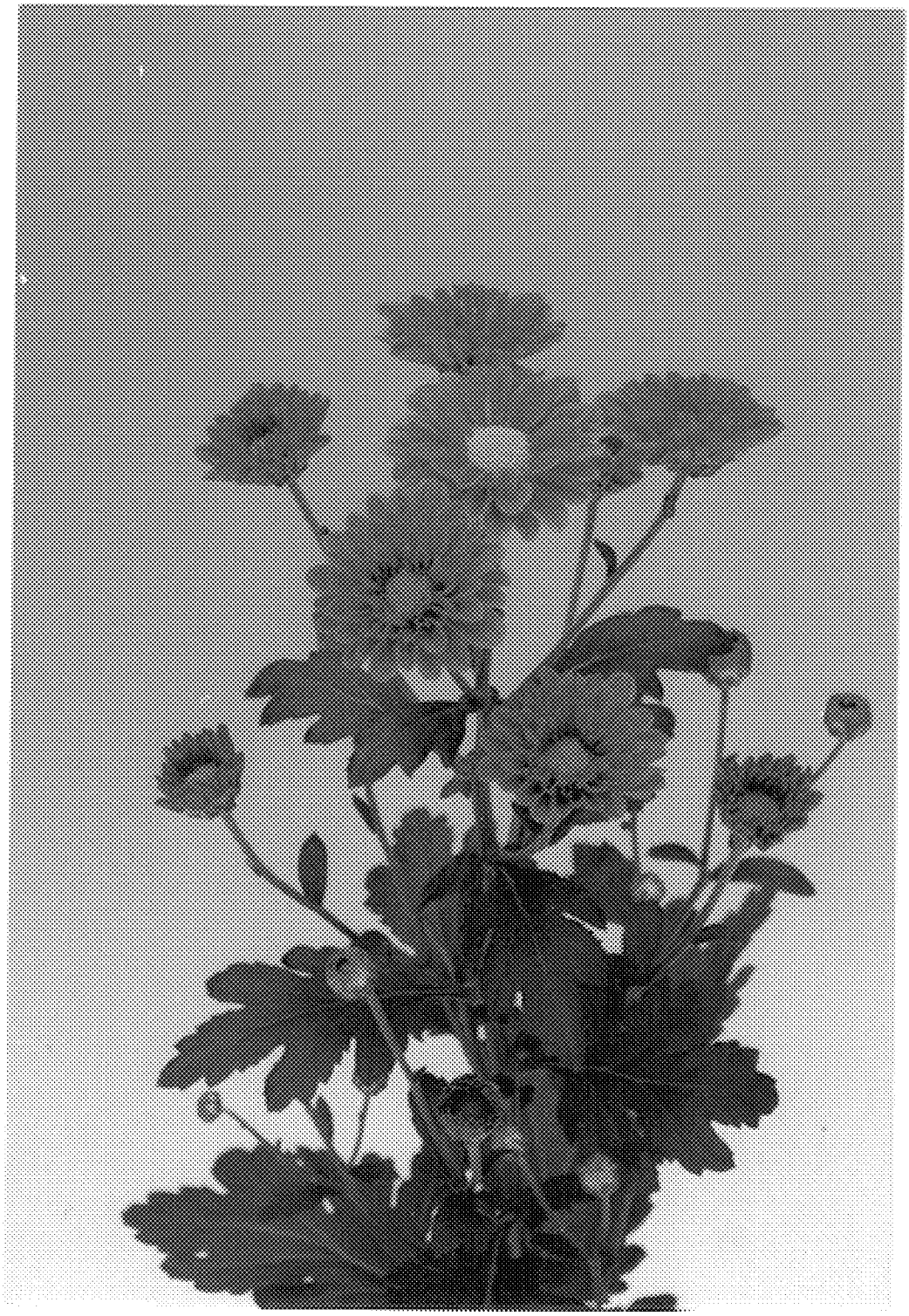
FIG. 1 shows the stem of the cultivar in full bloom.
Figure 2:
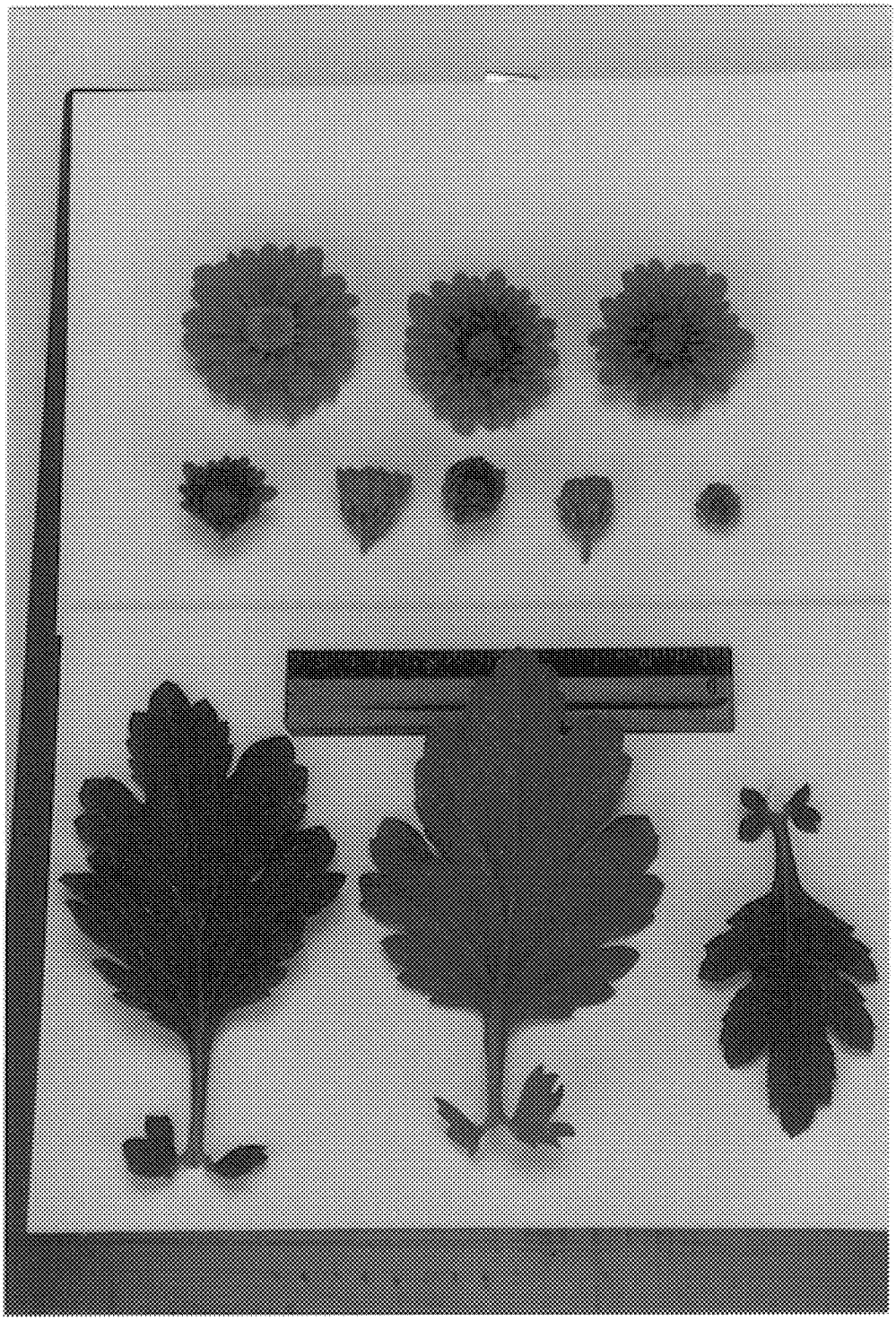
FIG. 2 shows the various stages of bloom and foliage of the new cultivar.

This new variety of chrysanthemum is of the botanical classification *Dendranthema grandiflora*. When grown in the vicinity of Ter Aar, Holland, it has a response time of approximately 8 weeks. This new variety produces small sized blooms with purple ray florets and green-yellow disc florets having a 3 week performance (i.e., vase life of 21 days). This new variety of chrysanthemum has been found to retain its distinctive characteristics throughout successive propagations. However, the phenotype may vary significantly with variations in environment such as light intensity and temperature. To show the phenotype as described Refocus and be planted year round under greenhouse conditions in Holland.

The following is a description of the plant and characteristics that distinguish Refocus as a new and distinct variety.

The color designations (color designations are from the R.H.S. Colour Chart) are taken from the plant itself. Accordingly, any discrepancies between the color designations and the colors depicted in the photographs are due to photographic tolerances.

Botanical Description of Refocus, Pink Refocus, Red Refocus and White Refocus

| CULTIVAR | REFOCUS |
|---|---|
| Bud | |
| Size | medium, cross section ± 1.2 cm, height ± 1.2 cm |
| Outside Color | red-purple 70A |
| Bloom | |
| Size | small |
| Fully Expanded | 4–4 1/2 cm |
| Borne | upper portion single flower per peduncle, lower portion plural flower per peduncle |
| Number of Blooms per single stem | average of 10 |
| Peduncle Lengths | near the top ± 10 cm, near the middle 20 cm, near the bottom 20 cm |
| Peduncle Lateral Shoot, Attachment | medium |
| Peduncle Lateral Shoot, Angle | 30°–35° |
| Form | single (daisy) |
| Performance (blooming period) | good, 21 days (18°–20° C.) |
| Color | |
| Center of Flower/disc floret | yellow-green 145A at an early stage of inflorescence, mature yellow-orange 14B |
| Color of upper surface of the majority of the ray-florets | red-purple 71C |
| Color of lower surface of the majority of the ray-florets | purple violet 80D |
| Tonality from Distance | a small purple daisy |
| Discoloration | ray florets to red-purple 72D |
| Pollen | yellow-orange 14A |

-continued

Botanical Description of Refocus, Pink Refocus, Red Refocus and White Refocus

| | |
|---|---|
| Ray florets | |
| Texture | upper side dmooth, under side smooth |
| Number | 35–40 (2–3 rows) |
| Cross-section | concave |
| Longitudinal axis of majority | straight |
| Shape of tip | pointed |
| Fragrance | typical chrysanthemum |
| Disc Diameter | small to medium (1.0–1.2 cm) |
| Reproductive Organs | |
| Stamen (present in disc florets only) | yellow-green, thin, ± 4 mm in length |
| Pollen | present, abundant |
| Styles (present in both ray and disc florets) | yellow-green, thin |
| Style length | ± 4 mm |
| Stigmas | yellow |
| Stigma Width | ± 1 mm |
| Ovaries | enclosed in calyx |
| Plant | |
| Growth | short to medium |
| Height | ± 95–100 cm |
| Stem color | yellow-green 146B |
| Stem Strength | strong |
| Stem Brittleness | present |
| Stem Anthocyanin Coloration | absent |
| Internodes | short (1.5–2.0 cm) |
| Flowering Response (photoperiodic controlled crop, no natural growing) | 8 weeks |
| Foliage | |
| Color | upperside yellow-green 147A<br>underside yellow-green 147B |
| Size | length 9 cm, width 6 cm |
| Quantity (per single stem) | 28–32 |
| Shape | egg-shaped |
| Texture | fleshy |
| Ribs and Veins | both ribs and veins well developed |
| Edge | crenated |
| Shape of Base of Sinus Between Lateral Lobes | round |
| Margin of Sinus Between Lateral Lobes | converging |
| Shape of Base | rounded |
| Apex | mucronate |
| Year of Discovery | 1992 |

| CULTIVAR | PINK REFOCUS |
|---|---|
| Bud | |
| Size | medium, cross section ± 1.2 cm, height ± 1.2 cm |
| Outside Color | red-purple 58B |
| Bloom | |
| Size | small |
| Fully Expanded | 4–5 cm |
| Borne | upper portion single flower per peduncle, lower portion plural flower per peduncle |
| Number of Blooms per single stem | average of 10 |
| Peduncle Lengths | near the top ± 10 cm, near the middle 20 cm, near the bottom 20 cm |
| Peduncle Lateral Shoot, Attachment | medium to strong |
| Peduncle Lateral Shoot, Angle | 30°–35° |
| Form | single (daisy) |
| Performance (blooming period) | good, 21 days (18°–20° C.) |

-continued

Botanical Description of Refocus, Pink Refocus, Red Refocus and White Refocus

| | |
|---|---|
| Color | |
| Center of Flower/disc floret | yellow-green 144B at an early stage of inflorescence, mature yellow-orange 14B |
| Color of upper surface of the majority of the ray-florets | near red-purple 58C |
| Color of lower surface of the majority of the ray-florets | red-purple 58C |
| Tonality from Distance | a small pink/purple daisy |
| Discoloration | ray florets to red-purple 58D |
| Pollen | yellow-orange 14A |
| Ray florets | |
| Texture | upper side dmooth, under side smooth |
| Number | 38–45 (3 rows) |
| Cross-section | concave |
| Longitudinal axis of majority | straight |
| Shape of tip | pointed |
| Fragrance | typical chrysanthemum |
| Disc Diameter | small to medium (1.0–1.2 cm) |
| Reproductive Organs | |
| Stamen (present in disc florets only) | yellow-green, thin, ± 4 mm in length |
| Pollen | present, abundant |
| Styles (present in both ray and disc florets) | yellow-green, thin |
| Style length | ± 4 mm |
| Stigmas | yellow |
| Stigma Width | ± 1 mm |
| Ovaries | enclosed in calyx |
| Plant | |
| Form | spray mum meant for erect culture. Herbaceous |
| Growth | short to medium |
| Height | ± 100–105 cm |
| Stem color | yellow-green 146B |
| Stem Strength | strong |
| Stem Brittleness | absent |
| Stem Anthocyanin Coloration | present |
| Internodes | short (1.5–2.0 cm) |
| Flowering Response (photoperiodic controlled crop, no natural growing) | 8 weeks |
| Foliage | |
| Color | upperside yellow-green 147A<br>underside yellow-green 147B |
| Size | length 9 cm, width 6 cm |
| Quantity (per single stem) | 28–32 |
| Shape | egg-shaped |
| Texture | fleshy |
| Ribs and Veins | both ribs and veins well developed |
| Edge | crenated |
| Shape of Base of Sinus Between Lateral Lobes | round |
| Margin of Sinus Between Lateral Lobes | converging |
| Shape of Base | rounded |
| Apex | cuspidate |
| Year of Discovery | 1993 |

| CULTIVAR | RED REFOCUS |
|---|---|
| Bud | |
| Size | Small, cross section ± 1.0 cm, height ± 1.0 cm |
| Outside Color | red 46B |

-continued

| Botanical Description of Refocus, Pink Refocus, Red Refocus and White Refocus | |
|---|---|
| Bloom | |
| Size | small |
| Fully Expanded | 4–4 1/2 cm |
| Borne | upper portion single flower per peduncle, lower portion plural flower per peduncle |
| Number of Blooms per single stem | average of 10 |
| Peduncle Lengths | near the top ± 10 cm, near the middle 20 cm, near the bottom 20 cm |
| Peduncle Lateral Shoot, Attachment | medium |
| Peduncle Lateral Shoot, Angle | 30° |
| Form | single (daisy) |
| Performance (blooming period) | good, 21 days (18°–20° C.) |
| Color | |
| Center of Flower/disc floret | yellow-green 144B at an early stage of inflorescence, mature yellow-orange 14B |
| Color of upper surface of the majority of the ray-florets | red 45A |
| Color of lower surface of the majority of the ray-florets | red 45C |
| Tonality from Distance | a small red daisy |
| Discoloration | ray florets to red 45C |
| Pollen | yellow-orange 14A |
| Ray florets | |
| Texture | upper side dmooth, under side smooth |
| Number | 35–40 (2–3 rows) |
| Cross-section | concave |
| Longitudinal axis of majority | straight |
| Shape of tip | pointed |
| Fragrance | typical chrysanthemum |
| Disc Diameter | small to medium (1.0–1.2 cm) |
| Reproductive Organs | |
| Stamen (present in disc florets only) | yellow-green, thin, ± 4 mm in length |
| Pollen | present, abundant |
| Styles (present in both ray and disc florets) | yellow-green, thin |
| Style length | ± 4 mm |
| Stigmas | yellow |
| Stigma Width | ± 1 mm |
| Ovaries | enclosed in calyx |
| Plant | |
| Form | spray mum meant for erect culture. Herbaceous |
| Growth | short to medium |
| Height | ± 95–100 cm |
| Stem color | yellow-green 146B |
| Stem Strength | strong |
| Stem Brittleness | absent |
| Stem Anthocyanin Coloration | present |
| Internodes | short (1.5–2.0 cm) |
| Flowering Response (photoperiodic controlled crop, no natural growing) | 8 weeks |
| Foliage | |
| Color | upperside yellow-green 147A underside yellow-green 147B |
| Size | length 10 cm, width 7 cm |
| Quantity (per single stem) | 28–32 |
| Shape | egg-shaped |
| Texture | fleshy |
| Ribs and Veins | both ribs and veins well developed |
| Edge | crenated |
| Shape of Base of Sinus | round |

-continued

| Botanical Description of Refocus, Pink Refocus, Red Refocus and White Refocus | |
|---|---|
| Between Lateral Lobes | |
| Margin of Sinus Between Lateral Lobes | converging |
| Shape of Base | rounded |
| Apex | mucronate |
| Year of Discovery | 1993 |
| CULTIVAR | WHITE REFOCUS |
| Bud | |
| Size | medium, cross section ± 1.5 cm, height ± 1.0 cm |
| Outside Color | yellow-orange 20D |
| Bloom | |
| Size | small |
| Fully Expanded | 3 1/2–4 cm |
| Borne | upper portion single flower per peduncle, lower portion plural flower per peduncle |
| Number of Blooms per single stem | average of 10 |
| Peduncle Lengths | near the top ± 10 cm, near the middle 20 cm, near the bottom 20 cm |
| Peduncle Lateral Shoot, Attachment | medium |
| Peduncle Lateral Shoot, Angle | 30°–35° |
| Form | single (daisy) |
| Performance (blooming period) | good, 21 days (18°–20° C.) |
| Color | |
| Center of Flower/disc floret | yellow-green 144A at an early stage of inflorescence, mature yellow-orange 14B |
| Color of upper surface of the majority of the ray-florets | pure white 155D (but whiter) |
| Color of lower surface of the majority of the ray-florets | pure white 155D (but whiter) |
| Tonality from Distance | a clear white small daisy |
| Discoloration | ray florets none, disc florets to yellow-orange 14B |
| Pollen | none |
| Ray florets | |
| Texture | upper side dmooth, under side smooth |
| Number | 22–26 (2 rows) |
| Cross-section | convex (no keels) |
| Longitudinal axis of majority | reflexing |
| Shape of tip | rounded |
| Fragrance | typical chrysanthemum |
| Disc Diameter | small to medium (1.2–1.5 cm) |
| Reproductive Organs | |
| Stamen (present in disc florets only) | yellow-green, thin, ± 4 mm in length |
| Pollen | not present |
| Styles (present in both ray and disc florets) | yellow-green, thin |
| Style length | ± 4 mm |
| Stigmas | yellow |
| Stigma Width | ± 1 mm |
| Ovaries | enclosed in calyx |
| Plant | |
| Form | spray mum meant for erect. Herbaceous |
| Growth | short to medium |
| Height | ±100–105 cm |
| Stem color | yellow-green 147B |
| Stem Strength | strong |
| Stem Brittleness | present |
| Stem Anthocyanin Coloration | present |
| Internodes | short (1.5–2.0 cm) |

-continued

| Botanical Description of Refocus, Pink Refocus, Red Refocus and White Refocus | |
|---|---|
| Flowering Response (photoperiodic controlled crop, no natural growing) | 8 weeks |
| Foliage | |
| Color | upperside yellow-green 147A<br>underside yellow-green 147B |
| Size | length 9 cm, width 6 cm |
| Quantity (per single stem) | 30–35 |
| Shape | egg-shaped |
| Texture | fleshy |
| Ribs and Veins | both ribs and veins well developed |
| Edge | crenated |
| Shape of Base of Sinus | round |

-continued

| Botanical Description of Refocus, Pink Refocus, Red Refocus and White Refocus | |
|---|---|
| Between Lateral Lobes | |
| Margin of Sinus Between Lateral Lobes | converging |
| Shape of Base | rounded |
| Apex | mucronate |
| Year of Discovery | 1995 |

I claim:

1. A new and distinct variety of chrysanthemum plant as described and illustrated.

* * * * *